United States Patent
Wang

(10) Patent No.: US 6,231,982 B1
(45) Date of Patent: May 15, 2001

(54) PARTICLE REAGENTS HAVING REDUCED MATRIX EFFECTS AND CONTAINING AN ALDEHYDE-REACTIVE FUNCTIONAL GROUP

(75) Inventor: Chengrong Wang, Hockessin, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 08/988,628

(22) Filed: Dec. 10, 1997

(51) Int. Cl.⁷ .................................................. B32B 5/16
(52) U.S. Cl. ..................... 428/407; 536/112; 536/121; 424/490; 424/493; 436/73; 436/86
(58) Field of Search ...................... 428/403, 407; 536/112, 121; 435/402; 424/489, 490, 493, 499; 436/73, 85

(56) References Cited

U.S. PATENT DOCUMENTS

| 4,452,773 | * | 6/1984 | Molday | 424/1.1 |
|---|---|---|---|---|
| 4,534,996 | | 8/1985 | Rembaum et al. | |
| 4,661,408 | | 4/1987 | Lau et al. | |
| 4,798,823 | | 1/1989 | Witzel. | |
| 4,801,504 | | 1/1989 | Burdick et al. | |
| 4,861,705 | | 8/1989 | Margel. | |
| 5,151,348 | | 9/1992 | Lau et al. | |
| 5,169,754 | | 12/1992 | Siiman et al. | |
| 5,169,773 | | 12/1992 | Rosenthaler et al. | |
| 5,239,057 | | 8/1993 | Wang et al. | |
| 5,248,772 | * | 9/1993 | Siiman et al. | 536/112 |
| 5,302,532 | | 4/1994 | Lau. | |
| 5,350,574 | | 9/1994 | Erlanger et al. | |
| 5,466,609 | * | 11/1995 | Siiman et al. | 436/518 |
| 5,527,713 | | 6/1996 | Bolton et al. | |
| 5,639,620 | * | 6/1997 | Siiman et al. | 435/7.21 |
| 5,707,877 | * | 1/1998 | Siiman et al. | 436/518 |

FOREIGN PATENT DOCUMENTS

| 0 487 289 A2 | 5/1992 | (EP). |
|---|---|---|
| 0 487 289 B1 | 9/1996 | (EP). |
| WO 90/06763 | 6/1990 | (WO). |
| WO 94/09368 | 4/1994 | (WO). |

OTHER PUBLICATIONS

Manabe, et al.; *J. Lab. & Clin. Med.*; Production of a Monoclonal Antibody–Methotrexate Conjugate Utilizing Dextran T–40 and its Biologic Activity; 104:445–454; Sep. 1984 (XP–002100335).

Papageorgiu, et al.; *Bioorganic & Medical Chemistry Letters*; Derivatives of Cyclosporin at Position 2 as Probes for Cyclophilin; vol. 3, No. 12, pp 2259–2564; 1993.

Rauffer, et al.; *Molecular Immunology;* Structure–Activity Relationships for the Interaction Between Cyclosporin A Derivatives and the Fab Fragment of a Monoclonal Antibody; vol. 31, No. 12, pp 913–922; 1994.

* cited by examiner

*Primary Examiner*—Hoa T. Le
(74) *Attorney, Agent, or Firm*—Lois K. Ruszala

(57) ABSTRACT

The invention is directed to the preparation of magnetic and non-magnetic particles coated with a polyaldehyde dextran material and a process for making the same. The polyaldehyde dextran coated particles of the invention are suitable for use in immunological assays and exhibit a reduced matrix effect in such assays when compared to convention particles without a polyaldehyde dextran coating.

10 Claims, No Drawings

PARTICLE REAGENTS HAVING REDUCED MATRIX EFFECTS AND CONTAINING AN ALDEHYDE-REACTIVE FUNCTIONAL GROUP

TECHNICAL FIELD

This invention relates generally to particles for use in immunological assays. Specifically, this invention relates to particles coated with a polyaldehyde dextran substance to reduce the matrix effect in immunological assays.

BACKGROUND OF THE INVENTION

The use of polymeric particles, including colloidal particles, either magnetic or non-magnetic, to bind a compound has long been known and used in industrial and laboratory procedures. For example, spherical polystyrene-divinylbenzene particles, Merrifield resins, were among the earliest and most widely used modern substrate particles. These particles found great utility in organic synthesis, in catalysis for heterogenizing homogeneous catalysts and in the biotechnical arts. Since these early particles were fairly large, they could easily be separated by filtration. However, in some fields, and particularly in the biochemical arts, it is desirable to use colloidal sized particles because the material being used is scarce, expensive, or is to be used in a procedure where larger particles cannot be used. When particles are of colloidal size, however, their separation from liquid medium can become a lengthy and difficult process because the colloidal particles tend to coat and plug the pores of filters. Consequently, magnetic colloidal particles are frequently used to avoid these difficulties.

The use of magnetic particles, specifically magnetic particles having a polymeric coating, has found great utility because such particles can be magnetically gathered to one side of a reaction vessel and the bulk of the reaction medium simply decanted. [As used herein, the words "particle" or "particulate substrate" or variation thereof encompasses spheres, spheroids, beads, and other shapes as well. These words are used interchangeably herein unless otherwise specified.] Magnetic particles are particularly useful in biological applications, especially where enzymes, antibodies and other substances are bound to the surface coating of the particles. The bound enzymes, antibodies or other substances may be used to capture a specific material from a sample in order to concentrate and analyze it, or to capture undesirable material from a sample, leaving the desired material in the sample for further use.

Practical considerations limit the usefulness of most polymer coated magnetic particles in medical and biological applications. Important factors for consideration are uniform particle size and shape, the need for the test reagent or sample to be tightly bound to the particle, the biodegradability of the particle or particle coating so that a test sample can be recovered, and the effect that the particle or particle coating will have on the test results when a sample is tested at various concentrations or in different mediums such as serum, whole blood or water to determine a standard curve or to assay the concentration of a substance in a test sample. Numerous types of particles, magnetic and non-magnetic, have been described in the patent and technical literature, and many are commercially available from sources well known to those skilled in the art. Examples of magnetic and non-magnetic particles may be found in U.S. Pat. Nos. 5,169,754; 5,248,772 and 5,527,713 (the '754, '772 and '713 patents, all to Simian et al.), and the references cited therein, all of which are incorporated herein by reference.

While commercially available particles and the particles described in these patents have been found to have utility in biological applications, particularly in immunological assays, such particles are also known to exhibit a "matrix effect" which places a severe limitation on the utility of such particles.

A "matrix effect" results when a sample is assayed in varying sample media, for example, serum, whole blood and water, or at varying concentrations in a single medium. Assays results can exhibit a matrix shift or a measurement bias dependent on the solution medium and/or concentration. In particular, the matrix effect results when particles are used to remove an excess of a reagent so that the remaining solution can be assayed for a particular species. Frequently, additional substances, often of an unknown nature, are also removed by the particles. This removal produces the variation or matrix effect and makes it extremely difficult to reproduce assay results or correlate the test or assay results on a day-to-day basis or from assay-to-assay performed on the same day The particles presently available have been found to exhibit this matrix effect. Consequently, it would be advantageous to have particles which minimize the matrix effect. The type of assays which would benefit from such a matrix effect minimizing substrate are generally known to those skilled in the art and examples can be found in U.S. Pat. Nos. 4,661,408 (the '408 patent) and 5,151,348 (the '348 patent), both to Lau et al.

Accordingly, it is an object of the invention to provide magnetic and non-magnetic particles suitable for use in immunological assays and compatible with biological substances.

It is a further object of the invention to provide magnetic and non-magnetic particles which, when used in immunological assays, minimize the matrix effect by selectively removing from a solution medium the species desired to be removed.

It is also an object of the invention to provide magnetic or non-magnetic particles suitable for use in immunological assays with antibodies, enzymes and similar biochemical substances.

SUMMARY OF THE INVENTION

The invention provides for magnetic and non-magnetic particles, including colloidal-sized particles, having a dextran or dextran-derived coating (herein, a "dextran coating") and suitable for use in immunological assays. The particles of the invention are prepared by first oxidizing dextran with selected oxidizing agents to obtain a dextran-derived substance having a plurality of pendent aldehyde groups, a polyaldehyde dextran, coupling the dextran-derived substance to a magnetic or non-magnetic particle having pendent amino groups or other functional groups reactive with aldehyde groups to obtain a dextran-coated particle useful in immunoassays. The particles so coated are suitable for use in immunological assays and exhibit a reduced matrix effect relative to conventional, commercially available particles without the polyaldehyde-dextran coating of the invention.

DETAILED DESCRIPTION OF THE INVENTION

The particles coated according to the invention may be of any size in the surface area range 10–100 $m^2/g$. For immunological assays, particles which have a surface area in the range of 10 to 60 $m^2/g$ are preferred. The particles may be magnetic or non-magnetic, magnetic particles being preferred due to the ease of separation they afford in immunological assays. An example of such magnetic particles include those which have a magnetic core surrounded by a polymeric material. The polymeric material may be any polymeric material suitable for use in immunoassays, polystyrene and polystyrene-divinyl benzene being preferred for their easy availability. Further, the polymeric material preferably either has functional groups reactive with aldehyde groups or can be modified by methods known in the art to contain such aldehyde-reactive groups. Examples of such functional groups include amine, hydrazine, hydrazide, aminooxy, cyanide and alcohol groups, amine groups being preferred.

If the particles are magnetic, the magnetic material contained in the particles may be any magnetic material susceptible to attraction by a permanent magnet or an electromagnet. Examples of such magnetic materials include magnetic iron oxides, magnetic chromium oxides, $MnFeO_4$, $ZnFeO_4$, $CoFe_2O_4$ and similar magnetic materials.

Another example of magnetic particles which may be used in practicing the invention are chromium oxide magnetic particles having pendent surface groups which are aldehyde-reactive or which can be modified to contain such aldehyde-reactive groups. Such magnetic chromium oxide particles include those comprising a core of $CrO_2$ which has a reduced surface which is then coated with silica and further coated with a silane as taught by Lau in the '408 patent. The outer silane layer is capable of binding proteins including antibodies and antigen species, ligands, haptens or linking compounds directly or through intermediate coupling agents to the coated core. Linking and/or coupling agents useful in practicing the invention include dicarboxylic acids and anhydrides, polyamines, polyaldehydes, and heterobifunctional agents such as 2-iminothiolane hydrochloride, sulfosuccinimidyl-4-(N-maleimidomethyl)cyclohexane-1-carboxylate, m-maleimidosuccinimide ester, N-succinimidyl-(4-iodoacetyl)aminobenzoate, and similar species known to those skilled in the art.

The dextran materials used in practicing the invention may be of any molecular weight, for example, from about 20,000 to about 2,000,000 daltons molecular weight. Such materials are commercially available.

In general, a polyaldehyde dextran is prepared by partial cleavage and oxidation of about 2% to about 20% of the glucopyranose rings in dextran. However, because the possibility of fracturing the polymeric structure of a dextran molecule increases as the number of rings oxidized increases, the percentage of rings oxidized is preferably about 2% to about 15%, and most preferably about 2% to about 10%.

Any oxidizing agent known to those skilled in the art as suitable for the partial cleavage and oxidation of the dextran glucopyranose rings may be used in practicing the invention. Examples of such oxidizing agents include perhalogenate compounds of formula $XO_4^{-1}$ where X=Cl, Br or I, ozone, peroxides and similar oxidizing agents. Sodium periodate is preferred. The quantity of oxidizing agent used in practicing the invention is based on the consideration that a single glucopyranose ring may be opened and oxidized to contain two aldehyde groups without fracturing of the bonds linking it to other glucopyranose rings in the dextran molecule. Consequently, care should be exercised in the ring cleavage/oxidation process in order to insure that excessive oxidation does not occur which might result in fracturing the dextran molecule into lower molecular weight species.

As a result of the partial oxidation, the resulting product contains glucopyranose rings linked together by linear derivatives of the rings which contain aldehyde groups, a polyaldehyde dextran material (PAD). The PAD material is reacted with a particulate substrate having aldehyde-reactive functional groups such as amines to yield a PAD-coated particulate substrate suitable for use in immunoassays. When used in such assays, these PAD-coated particles produce a reduced or minimized matrix effect relative to similar particles which have not been coated with PAD. The PAD coated particles of all types, whether magnetic or non-magnetic, polymeric in nature such as polystyrene latex beads or non-polymer in nature such as the magnetic chromium oxide particles described above, are capable of binding proteins including antibodies and antigen species, ligands, haptens or linking compounds directly or through intermediate coupling agents.

The following examples are given by way of illustrating the invention and are not to be taken as limiting the invention. For example, a dextran of 2,000,000 molecular weight can be used in place of the 40,000 molecular weight dextran used in the examples. As used herein, the term water refers to deionized or distilled water.

Preparation of Polyaldehyde Dextran

Sixteen grams of 40,000 molecular weight (MW) dextran is dissolved in approximately 60 ml of deionized water and 2.1143 g (9.88 mmol) sodium periodate ($NaIO_4$) is added with stirring at room temperature (about 18–30° C.). The ratio of dextran to $NaIO_4$ used in the reaction is about 10:1. After the addition of the sodium periodate is completed, the reaction mixture is stirred overnight, approximately 12–20 hours, at room temperature. The reaction mixture is then dialyzed three times against four liters of water. After dialysis, the resulting dialyzed polyaldehyde dextran (PAD) containing solution is lyophilized to obtained dry polyaldehyde dextran.

The degree of polyaldehyde formation and the percentage of dextran rings opened can be determined by use of a standard containing methyl orange and hydroxylamine hydrochloride. To prepare the standard, 4.375 g dry hydroxylanine hydrochloride and approximately 1 mg methyl orange are placed in a 250 ml volumetric flask. Approximately 200 ml deionized water are added; and the contents of the flask are swirled until the hydroxylamine hydrochloride and methyl orange are dissolved. The pH of the resulting solution is adjusted to about 4 using a solution of hydrochloric acid or sodium hydroxide to yield a solution having a color between red and yellow, that is, an orange color. The volume of the resulting solution is then adjusted to 250 ml using deionized water to obtain a 0.25 N (Normal), orange colored hydroxylamine solution.

The degree of aldehyde substitution present on the PAD product is determined by dissolving 100 mg of the lyophilized PAD material in 25 ml of the 0.25 N hydroxylamine hydrochloride standard solution. The resulting solution is allowed to stand at room temperature for about 2 hours to insure that the PAD material is completely dissolved and a red color develops. The solution is then titrated using 0.0100 N NaOH until the color of the PAD-containing solution matches the orange color of the 0.25 N hydroxylamine hydrochloride standard solution. The degree of aldehyde substitution can then be calculated using the formula:

$$D=[V \times C \times MW] \div 100$$

where:
1. D equals the degree of substitution in percent;
2. V equals the volume of 0.0100 N NaOH used in adjusting the color of the PAD-containing hydroxylamine hydrochloride solution;

3. C is 0.0100, the concentration of the NaOH solution; and
4. MW is the molecular weight of the dextran starting material which in the examples herein is 40,000.

In the above example, it was determined that about 5% of the dextran glucopyranose rings were oxidized to generate about 24 aldehyde groups per molecule.

Preparation of PAD-Chrome Particles.

Magnetic chrome particles with pendent amine groups such as those described in the '408 patent were obtained from the DuPont Company and were washed three times with a suitable phosphate buffered saline solution (PBS) such as the 1×PBS described in the '713 patent at column 10, lines 42–45, or PBS as described in the '348 patent at column 6, lines 2–4. After washing, the chrome particles were diluted with PBS to 5% w/v. A 9.045 g sample of PAD (40,000 MW, 5.43 mmol —CHO groups) and 0.845 g NaCNBH$_3$ (13.5 mmol) was dissolved in PBS and 150 ml of the 5% w/v chrome particle solution was added to the PAD solution. The reaction mixture was mechanically rotated at room temperature for about 48 hours. The particles were then magnetically held to the side of the reaction vessel, the reaction solution decanted, and the particles washed three times with PBS and three times with water. Alternatively, a preferred method of centrifugation at about 2,000 to about 5,000 rpm, preferably at about 3,300 to about 3,500 rpm, and decantation of supernatant liquid can be used. The resulting PAD-Chrome particles were then diluted with 60 ml water to 5% w/v.

The PAD-Chrome particles prepared as described were used in an immunological assay for the measurement of cyclosporin A in whole blood or serum samples. To perform the assay, a 60 ml 5% w/v sample of PAD-Chrome particles are first activated by the addition of 0.5885 g NaIO$_4$ to the PAD-Chrome solution. The resulting mixture is mechanically rotated overnight, about 12–20 hours, at room temperature. After rotation is completed, the particles are magnetically held in the reaction vessel, the solution decanted, the particles washed three times with PBS and three times with water, and finally diluted with PBS to produce 60 ml of particle solution which is 5% w/v.

Preparation of Cyclosporin C-CA-IgG for Binding to PAD-Chrome Particles.

In a separate procedure, cyclosporin C was derivatized with a dicarboxylic acid or dicarboxylic acid anhydride by methods known to those skilled in the art to form a cyclosporin C-hemidicarboxylic acid derivative, CsC-CA, similar to the cyclosporin C-hemisuccinate described in the '348 patent at column 4, lines 28–34. [Note: Cyclosporin A may also be used in the method, but it is more difficult to derivatize because it has only a single hydroxyl group which is sterically hindered. Cyclosporin C has two hydroxyl groups, one of which is sterically hindered as in cyclosporin A and one of which is not sterically hindered. This difference does not affect the immunological assay test results. One can replace the cyclosporin C used in these examples with cyclosporin A.] The CsC-CA species was then coupled to a protein such as albumin or a globulin by methods known to those skilled in the art. CsA-CA was coupled to IgG to form CsA-CA-IgG conjugate suitable for coupling to a substrate.

In a preferred method, cyclosporin C was first derivatized with a diamine and then with a dicarboxylic acid or dicarboxylic acid anhydride by methods known to those skilled in the art to form a cyclosporin C-diamine-hemicarboxylic acid derivative, CsC-DA, similar to the CsC-CA species described above and the cyclosporin C-hemisuccinate described in the '348 patent at column 4, lines 28–38. The CsC-DA species was then conjugated to IgG as described above and ultimately to PAD-Chrome to form CsC-DA-IgG-PAD-Chrome. The use of the diamine to form the CsC-DA species is the subject matter of copending United States patent application entitled "Cyclosporine Derivatives and Uses Thereof", Ser. No. 08/978,051, filed on Nov. 25, 1997, now U.S. Pat. No. 5,990,274.

It is here noted that both CsC-DA-IgG-PAD-Chrome particles and CsC-CA-PAD-Chrome particles result in a reduced matrix effect relative to non-PAD containing particles, e.g., CsC-CA-IgG-Chrome. The data presented herein was obtained using CsC-DA-IgG-PAD-Chrome particles of the invention and CsC-CA-IgG-Chrome particles of the prior art.

The dicarboxylic acids and acid anhydrides may be selected from the group consisting of malonic, succinic, glutaric, adipic, maleic, fumaric, phthalic, isophthalic and terephthalic acids or anhydrides, and similar species. The acid anhydrides are preferred.

The diamine used to prepare CsC-DA can be any diamine of general formulas H$_2$NCH$_2$—(CH$_2$)$_x$—CH$_y$—(CH$_3$)$_z$—NH$_2$ and C$_6$H$_{4+a}$(NH$_2$)$_2$, where x=0–3, y=1 or 2, and z=1 when y=1 or z=0 when y=2; and a=0 or 6. Examples include ethylenediamine, phenylenediamine, propylenediamine, 1,4-cyclohexanediamine, tetramethylenediamine and similar diamine compounds. In addition, other polyamines may also be used in practicing the invention. Examples of such additional polyamines include, but are not limited to, diethylene triamine, 1,5-diamino-3-(2-aminoethyl)pentane and similar polyamines. Further, amine-containing ether compounds may also be used in practicing the invention. Examples of such compounds, but not limiting such, include ethylene glycol-bis-(2-aminoethyl)ether, ethylene glycol-bis-(3-aminopropyl)ether and similar compounds known to those skilled in the art.

Binding CsC-DA-IgG to PAD-Chrome Particles.

PAD-Chrome magnetic particles were washed three times with PBS prior to reaction with the CsC-DA-IgG conjugate. After washing, a 150 ml aqueous solution of 5% w/v PAD-Chrome particles was prepared and a 150 ml solution containing 300 mg of CsC-DA-IgG was added to the PAD-Chrome solution. After the addition of the CsC-DA-IgG solution, 168 mg of NaCNBH$_3$ was added and resulting reaction mixture was mechanically rotated at cold room temperature, about 4° C., for about 48 hours. After rotation, 120 ml 30% aqueous bovine serum albumin (BSA) and 240 mg NaCNBH$_3$ was added to the reaction mixture and the resulting mixture mechanically rotated for an additional 16–20 hours. The coupling or conjugation reaction was then quenched by the addition of 420 ml of 2 M Glycine buffer to the reaction mixture followed by mechanical rotation for about 1 hour. The derivatized PAD-Chrome magnetic particles were then held to a side of the reaction vessel by use of a handheld magnet, the reaction solution decanted, and the particles washed three times with water, three times with methanol and three times with PBS buffer. Alternatively, the particles were separated by centrifugation as described herein, with the supernatant liquid being decanted. After the last buffer washing, the particles were diluted with 150 ml of PBS to give a 5% w/v solution of CsC-DA-IgG-PAD-Chrome particles designated Sample No. 40-101A.

Cyclosporin C-Chrome Particle Without PAD.

For comparison with the CsC-DA-IgG-PAD-Chrome particles of the invention, CsC-CA-IgG-Chrome particles having no PAD coating on the chrome particles were prepared and were designated as Sample No. 66-37. These particles were prepared by reacting magnetic chrome particles having pendent amine groups with glutaraldehyde followed by reaction with the CsC-CA-IgG species to generate CsC-CA-IgG-Chrome particles. The two types of particles were compared in an immunoassay for cyclosporin A using methods and procedures known to those skilled in the art, for example, as given in the '348 patent.

Cyclosporin A Assay.

Cyclosporin A containing samples were obtained from;

Sample A: Ciba-Corning (frozen liquid TDM L2, Lot 952051), nominal cyclosporin was not given;

Sample B: Baxter Dade (Immunoassay Control L1, Lot IAC-116M), nominal cyclosporin A value of 11–46 ng/ml;

Sample C: BioRad (human whole blood control, Lot 73032 L2), and nominal cyclosporin A value of 126–196 ng/ml; and Sample D Baxter Dade (TMD Plus XL, Lot TDL2-206), nominal cyclosporin A value of 147–175 ng/ml.

The cyclosporin A containing cells in the samples were lysed by methods known to those skilled in the art to release the cyclosporin A; for example, by lysing with a detergent.

A standard solution of anti-cyclosporin A antibody labeled with β-D-galactosidase was prepared according to methods known to those skilled in the art. The concentration of anti-cyclosporin A-β-D-galactosidase in the standard solution was about 0.1 to about 3 mg/ml. The standard solution was diluted 1:100 or 1:300, standard-to-water, for use in the immunological assays. The anti-cyclosporin A-B-D-galactosidase conjugate is designated CGC (cyclosporin-glactosidase conjugate). The anti-cyclosporin antibody can be polyclonal or monoclonal and can either be commercially obtained or prepared according to known methods. The monoclonal antibody is preferred.

The enzyme-linked immunoassay for cyclosporin A was performed according to methods known to those skilled in the art. In general, the procedures used to demonstrate the utility of the invention follow those described in the '348 patent. For example, an excess quantity of CGC was added to the cyclosporin A containing samples obtained from the lysed cells, Samples A through D, and the resulting mixture was incubated for a time in the range of 0.5–20 minutes, generally 1–5 minutes. After incubation, each sample was divided into two parts and a quantity of PAD-Chrome particles 40-101A were added to one part and non-PAD particles 66-37 (i.e., Chrome particles) were added to other part. The resulting solutions were incubated for about 1–10 minutes to allow unbound CGC to bind to the particles. The particles were magnetically held to a side of the reaction vessel and the reaction solution decanted. The resulting reaction solution was then immunoassayed for cyclosporin A using either chlorophenol red-β-D-galactosidase (CPRG) or resorufin-β-D-galactosidase (ReG) as a β-D-galactosidase substrate to produce a chromophore.

Alternatively, solid support columns containing either CsC-DA-IgG-PAD-Chrome particles or CsC-CA-IgG-Chrome were prepared as described in the '348 patent. One pair of for each of the Samples A through D. Excess CGC was added to each sample and the sample incubated as described. After incubation, the sample was injected into a clinical analyzer such as described in the '348 patent, eluted through the column as described and collected. After elution, β-D-galactosidase substrate was added to the solution and the absorbance measured at 577 nm.

In order to obtain a standard curve for the test results comparing PAD-Chrome particles and Chrome particles, a whole blood sample was prepared containing 0, 125, 350, 700 and 1100 ng/ml cyclosporin A. These samples were immunoassayed as described using CGC and the results are given in Tables 1 and 2. The results in Tables 1 and 2 indicate that whole blood samples treated with with PAD-Chrome particles 40-101A of the invention give a greater separatory response relative to samples treated with the Chrome particles 66-37 of the prior art. It is believed that the improved separation of the response is due to the fact that the PAD-Chrome particles are more selective, removing the CGC and little other substances relative the Chrome particles of the prior art.

TABLE 1

Cyclosporin A results using 1:300 CGC Dilution

| Cyclosporin A | mA/min | |
|---|---|---|
| ng/ml | Chrome Particles[1] | PAD-Chrome Particles[2] |
| 0 | 107 | 83 |
| 125 | 126 | 137 |
| 350 | 153 | 226 |
| 700 | 183 | 301 |
| 1100 | 204 | 333 |

Note:
[1]Chrome particles are sample 66-37.
[2]Pad-Chrome is sample 40-101A

TABLE 2

Cyclosporin A results using 1:100 CGC Dilution

| Cyclosporin A | mA/min | |
|---|---|---|
| ng/ml | Chrome Particles[1] | PAD-Chrome Particles[2] |
| 0 | 256 | 161 |
| 125 | 327 | 373 |
| 350 | 427 | 646 |
| 700 | 529 | 861 |
| 1100 | 585 | 970[3] |

Note:
[1]Chrome particles are sample 66-37.
[2]Pad-Chrome is sample 40-101A
[3]Monochromatic, mA/min is approximately 1200.

After the initial testing with cyclosporin A spiked whole blood samples, the PAD-Chrome particles and the Chrome particles of the prior art were used in bioassays with the cyclosporin A containing samples A through D. These bioassays were conducted as described herein and in the '348 patent, and the test results are shown in Table 3. The results indicate that when a single blood source has been treated with PAD-Chrome particles to remove excess CGC, the matrix effect seen between CGC dilutions of 1:300 and 1:100 is minimized. For example, for blood sample A from Ciba-Corning and PAD-Chrome particle to remove excess CGC, the difference in the assay between using 1:300 and 1:100 CGC (91.8−66.2=25.6) is smaller than the difference for the same assay when conventional Chrome particles are used to remove excess CGC (209.3−95.6=113.7). The fact that assay results are not the same at both dilutions indicates that when the particles are added to the test sample to remove excess CGC, they also remove some unknown substance which thereby effects the test results. However, the results also indicate that the PAD-Chrome particles of the invention minimize this matrix effect.

TABLE 3

Comparison PAD-Chrome Particles With Conventional Chrome Particles

| Sample | Particle | 1:300 CGC mA/min | 1:100 CGC mA/min | mA/min[1] (1:300–1:100) |
|---|---|---|---|---|
| A | PAD-Chrome[2] | 91.8 | 66.2 | 25.6 |
|   | Chrome[3] | 209.3 | 95.6 | 113.7 |
| B | Pad-Chrome | 6.6 | 46.3 | 39.7 |
|   | Chrome | 6.3 | −88.9 | 95.2 |
| C | PAD-Chrome | 99.5 | 98.0 | 1.5 |
|   | Chrome | 205.7 | 147.5 | 58.2 |
| D | PAD-Chrome | 87.5 | 74.7 | 12.8 |
|   | Chrome | 16.3 | 98.8 | 85.5 |

Note:
[1] "mA/min" (1:300–1:100) is the absolute value of the difference in the absorbance rate for a single blood sample and particulate substrate using two different dilutions of CGC.
[2] PAD-Chrome is particle sample 40-101A.
[3] Chrome is particle sample 66-37.

I claim:

1. Particle reagents exhibiting a reduced matrix effect in immunological assays, said particle reagents comprising magnetic or non-magnetic particles containing aldehyde-reactive functional groups and comprising a polyaldehyde dextran coating, said coating formed by the covalent bonding between a polyaldehyde dextran substance and the aldehyde-reactive functional groups.

2. The particle reagents according to claim 1 wherein the particle is a magnetic particle comprising a core of magnetic material, a polymeric material coating the magnetic core, and aldehyde-reactive functional groups pendent from the polymeric material.

3. The particle reagents according to claim 1 wherein the particle is a magnetic particle comprising a chromium oxide core, having undergone reduction of a portion of the chromium oxide a silica coating, and a silane coating having aldehyde-reactive functional groups or capable of being derivitized to contain aldehyde-reactive functional groups.

4. The particle reagents according to claim 1 wherein the polyaldehyde dextran has a molecular weight of about 20,000 to about 2,000,000 daltons.

5. The particle reagents according to claim 4 wherein the polyaldehyde dextran is prepared by partial cleavage and oxidation of dextran glucopyranose rings, the number of partially cleaved and oxidized rings in said polyaldehyde dextran being from about 2% to about 20%, and the molecular weight of the polyaldehyde dextran remain substantially the same.

6. The particle reagents according to claim 1 wherein the particle reagents further comprise an antigen, antibody, protein, hapten, ligand, and linking compounds bound to the polyaldehyde dextran coating directly or through intermediate coupling agents.

7. Polyaldehyde dextran coated magnetic chromium oxide particle reagents exhibiting a reduced matrix effect in immunoassays comprising a core of magnetic chromium oxide, having undergone reduction of a portion of the chromium oxide, and coated with one or a plurality of coatings ending with a coating have aldehyde-reactive functional groups, and a polyaldehyde dextran material bound to said chromium oxide particles by covalent reaction between the dextran aldehyde groups and the aldehyde-reactive groups.

8. The particle reagents according to claim 7 wherein the polyaldehyde dextran material has a molecular weight of about 20,000 to about 2,000,000 daltons.

9. The particle reagents according to claim 7 wherein the polyaldehyde dextran is prepared by partial cleavage and oxidation of dextran glucopyranose rings, the number of partially cleaved and oxidized rings in said polyaldehyde dextran being from about 2% to about 20% and the molecular weight of the polyaldehyde dextran remain substantially the same.

10. The particle reagents according to claim 7 wherein the particles further comprise an antigen, antibody, protein, hapten, ligands, and linking compounds bound to the polyaldehyde dextran coating directly or through intermediate coupling agents.

* * * * *